United States Patent [19]

Bewick

[11] Patent Number: 4,565,782

[45] Date of Patent: Jan. 21, 1986

[54] PROCESS FOR PRODUCING OPTICALLY ACTIVE ARYLOXYPROPIONIC ACIDS AND DERIVATIVES THEREOF USEFUL AS HERBICIDES

[75] Inventor: David W. Bewick, Bracknell, England

[73] Assignee: Imperial Chemical Industries PLC, London, England

[21] Appl. No.: 634,491

[22] Filed: Jul. 26, 1984

[30] Foreign Application Priority Data

Jul. 27, 1983 [GB] United Kingdom ............. 8320222
Nov. 1, 1983 [GB] United Kingdom ............. 8329086

[51] Int. Cl.$^4$ .................... C12P 17/12; C07P 41/00
[52] U.S. Cl. .................... 435/122; 435/119; 435/120; 435/121; 435/128; 435/130; 435/135; 435/136; 435/141; 435/146; 435/280
[58] Field of Search ............. 435/280, 119, 120, 121, 435/128, 130, 135, 136, 141, 146

[56] References Cited

U.S. PATENT DOCUMENTS 4,204,044  5/1980  Suhara et al. .................... 435/280
4,443,548  4/1984  Oshima et al. .................... 435/280
4,461,835  7/1984  Sih .................................... 435/280

FOREIGN PATENT DOCUMENTS 58-126792  7/1983  Japan.

OTHER PUBLICATIONS

Hutt et al., J. Pharm. Pharmacol., 1983, 35, 693–704.

Primary Examiner—Sam Rosen
Attorney, Agent, or Firm—Cushman, Darby & Cushman

[57] ABSTRACT

A process for the stereospecific inversion of the [S] enantiomer of an α-aryloxypropionic acid of formula I:

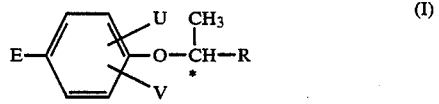

wherein E is $OR^1$ or

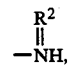

$R^1$ is an unsubstituted or substituted aryl or heterocyclic ring system, and $R^2$ is hydrogen or methyl, U and V each independently represent hydrogen or halogen and R is a carboxyl group, or an enzymic and herbicidal equivalent thereof, which process comprises contacting said [S] enantiomer with a microorganism having a stereospecific inverting enzyme system, or with an extract of the microorganism containing said enzyme system, to convert the [S] enantiomer to the corresponding [R] enantiomer.

13 Claims, No Drawings

PROCESS FOR PRODUCING OPTICALLY ACTIVE ARYLOXYPROPIONIC ACIDS AND DERIVATIVES THEREOF USEFUL AS HERBICIDES

This invention relates to a stereoselective process for producing individual isomers of optically active compounds, to a micro-organism and to further processing of the isomers.

The compounds to be prepared in the form of one enantiomer by the present process are α-aryloxypropionic acids and their enzymic and herbicidal equivalents (as hereinafter defined).

Previously known commercial methods for producing a single isomer of a compound involved physical, chemical or microbiological techniques. Physical techniques have relied on different physical properties of the isomers in a racemic mixture, eg. different crystallisability (though this is not appropriate to strict enantiomers), chemical techniques have relied on resolution of the chiral centre during production, eg. using a chiral catalyst, while microbiological techniques have generally relied on the use of micro-organisms or their enzymes which are either capable of synthesising the desired isomer or are capable of separating a racemate eg. by chemically modifying one of the isomers such as by degradation of one. In many cases, these techniques have been applied to compounds very early in the route for producing the desired product thereby running the risk that racemisation may occur during one of the subsequent process steps in the route.

It has now been found in accordance with the present invention, that α-aryloxypropionic acids may be stereospecifically "resolved" by means of a microbiological system. In the operation of this system, the [S] enantiomer is inverted to form the [R] enantiomer, while the [R] enantiomer itself remains substantially unaltered. This process thus achieves enrichment of the [R] enantiomer from a racemic mixture rather than separation and wasteful loss of the [S] enantiomer.

Accordingly, the present invention provides a process for the stereospecific inversion of the [S] enantiomer of an α-aryloxypropionic acid of formula I:

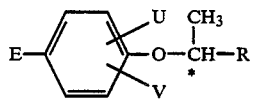
(I)

wherein E is OR¹ or

$R^1$ is an unsubstituted or substituted aryl or heterocyclic ring system and $R^2$ is hydrogen or methyl, U and V each independently represent hydrogen or halogen and R is a carboxyl group, or an enzymic and herbicidal equivalent thereof, which process comprises contacting said [S] enantiomer with a microorganism having a stereospecific inverting enzyme system, or with an extract of the microorganism containing said enzyme system, to convert the [S] enantiomer to the corresponding [R] enantiomer.

α-Aryloxypropionic acids to which the present process may be applied are disclosed eg. in European patent applications publication Nos. 0001473, 0000483, 0003114, 0023785, 0060607, 0029319, 0063866, 0024931, 0002800, 0075840 and Belgian Pat. No. 876077, the disclosures of which applications are incorporated herein by reference.

Particularly valuable examples of α-aryloxypropionic acids to which the present process may be applied are of formula:

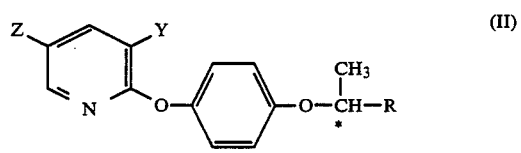
(II)

wherein Z and Y each represent fluorine, chlorine, bromine, iodine or hydrogen or a trifluoromethyl, difluoromethyl or chlorodifluoromethyl group provided that at least one of Z and Y is a halogenomethyl group or both Z and Y represent chlorine, and R represents a carboxyl group,

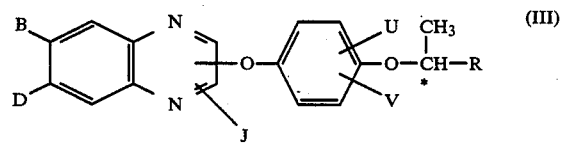
(III)

and

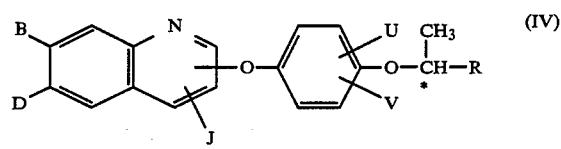
(IV)

wherein B, D, J, U and V each represent hydrogen or halogen and R is as defined above;

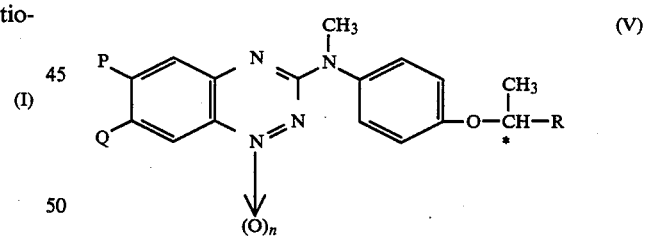
(V)

wherein one of P and Q represents halogen or trifluoromethyl and the other represents hydrogen, n is 0 or 1 and R represents a carboxyl group;

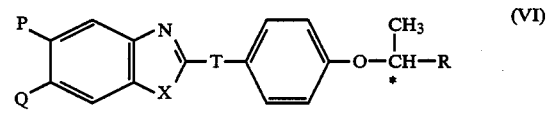
(VI)

wherein X represents —O— or —S—, P, Q and R are as defined above and T represents —O— or

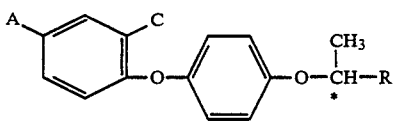

wherein A represents halogen or trifluoromethyl, C represents hydrogen, halogen or nitro and R is as defined above;

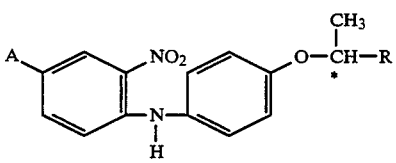

wherein A and R are as defined above;

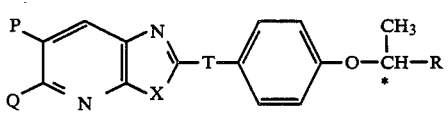

wherein P, Q, X, T and R are as defined above.

The asterisk indicates the chiral centre of these compounds.

In the compounds of formula II, preferably Z is trifluoromethyl and Y is hydrogen, chlorine or fluorine.

In the compounds of formula III and IV, preferably one of B and D is halogen eg. chlorine or fluorine and the other hydrogen, J is hydrogen and either U and V are both hydrogen or one is halogen eg. chlorine or fluorine, preferably in the 2-position, and the other is hydrogen. Desirably, when the quinoxaline or quinoline moiety is linked to the oxygen at the 2-position, B is hydrogen and D (6-position) is halogen, while when it is linked at the 3-position, D is hydrogen and B (7-position) is halogen.

In the compounds of formula V one of P and Q is preferably halogen eg. chlorine, particularly Q (7-position) and n is preferably 1.

In the compounds of formula VI, one of P and Q is preferably halogen eg. chlorine, particularly Q (6-position) when T is —O— and P (5-position) when T is

In the compounds of formula VII, A and C are preferably both halogen eg. chlorine or A is halogen eg. bromine and C is nitro or A is trifluoromethyl and C is hydrogen or halogen eg. chlorine.

In the compounds of formula VIII, A is preferably trifluoromethyl.

In the compounds of formula IX, one of P and Q is preferably halogen eg. chlorine, particularly Q (5-position) when T is —O— and P (6-position) when T is

In general, preferred $R^1$ groups have up to 20 eg. 3 to 10 carbon atoms and 0 to 6 eg. 0 to 3 heteroatoms such as O, N or S. Examples are: optionally substituted phenyl, pyridyl, quinazolinyl, quinolinyl, benztriazinyl-(—N—oxide), benzthiazolyl and benzoxazolyl, in particular those $R^1$ groups in formulae II to IX above. U and V as halogen are preferably chlorine or fluorine.

While it is possible to cary out the process of the invention using an [S] enantiomer in the substantial absence of the [R] enantiomer, the [S] enantiomer will normally be provided as part of the racemate of the particular α-aryloxypropionic acid or equivalent compound. As the enzyme system is stereoselective for the [S] enantiomer and the [R] enantiomer is not significantly altered by it, the resulting mixture is enriched in respect of the active [R] enantiomer. Thus, the resulting product formed from the racemate will certainly contain at least 50% of the [R] enantiomer and will normally contain at least 75%, preferably at least 90% up to, in theory, 100% of the [R] enantiomer.

The inversion is performed in the presence of the stereospecific inverting enzyme system which may, if desired, be completely or partially extracted from the micro-organism in which it occurs (ie. in pure or crude form) and may optionally be immobilised. However, it is preferred that the enzyme is present together with at least some of the cellular components of the micro-organism to obviate the need for special separation steps and enzyme purification and/or enzyme immobilisation procedures. The enzyme must be provided in an active and stable form in which the reaction will proceed and, when present in association with the cells, these may in theory be live or dead and be intact, detergent-treated, autolysed or immobilised cells. If desired the detergent-treated autolysed or immobilised cells may be homogenised. Particular methods of immobilising microbial cells include: binding to water-insoluble ion exchangers, via ionic bonds; cross-linking of the cells with a bifunctional reagent eg. glutaraldehyde; entrapping into a natural or synthetic polymer matrix where they are physically restrained, eg. using polyacrylamide, collagen, cellulose triacetate, agar, alginate such as calcium alginate, or polystyrene; binding to membrane reactors; liquid membrane encapsulation; polyelectrolyte flocculation; heat treatment and irradiation. (Polyelectrolyte flocculation followed by centrifugation, primary drying, extruding and secondary (fluidised bed) drying constitutes a particularly valuable method of obtaining immobilised cells in a useful form). Any of these methods which do not in any particular instance destroy the activity of the inverting enzyme system may be used. It is also desirable that the chosen method should not result in leakage of the enzyme from out of the microbial cells where these have been retained intact.

Reference is made above to "an enzyme system" to cover the enzyme or enzymes needed for the reaction or reactions which achieve inversion and the possibility of other substances present in the intact micro-organism eg. cofactors or coenzymes such as NADH or metal ions being required for efficient operation of the enzyme.

Reference is made herein to "enzymic and herbicidal equivalents" of the α-aryloxypropionic acids to encompass those derivatives where for example the carboxylic group is modified, eg. to salt form, which are equally well recognised by the microbial enzyme system and are themselves active herbicides. The present process may also operate in respect of esters eg. the $C_1$-$C_6$, preferably $C_1$-$C_4$, alkyl esters of the compounds of formula I provided hydrolysis to the acid eg. in the presence of other microbial enzymes, can be prevented. Particularly preferred esters are the methyl, n-butyl and ethoxyethyl esters of the acids of formula II when one of Z and Y is a halogenomethyl group and the propargyl ester of the acids of formula II when Z and Y are both chlorine; the ethyl or n-propyl ester of the acids of formulae III and IV; the isopropyl ester of the acid of formula V; the methyl and ethyl esters of the acids of formulae VI, VII and VIII and the methyl, ethyl and butyl esters of the acids of formula IX. Also preferred are compounds of formula II to IX with slight changes in substitution, particularly in the rings, where these substituents do not alter substantially the enzyme recognition and the herbicidal activity or function of the compound.

The inversion reaction occurring in the process of this invention has been deduced from observations made in soil from many parts of the world. Many different soil micro-organisms may therefore potentially possess the ability to carry out the inversion.

Particularly preferred for this process are bacteria, especially the Actinomycetales and related organisms in particular the Rhodococci, though it is also possible to use fungi.

A particular micro-organism isolated from a mixed culture of soil organisms grown on Nutrient agar and found to have the necessary properties for carrying out the inversion, is a Rhodococcus sp. and was deposited under the Budapest Treaty at the National Collections of Industrial and Marine Bacteria (NCIMB) Aberdeen, Scotland, on July 13, 1983 and given accession No. NCIB 11880.

The general characteristics of the strain NCIB 11880 are:

1. Microscopic cell morphology
(a) When grown for 18 hours at 30° C. on CMI+0.75% Nutrient agar and viewed by phase contrast:
   Shape—rod shaped with some branching.
   Association—cells are aggregated.
   Gram strain—gram positive.
   Spores—not produced.
   Motility—none, no flagella.
(b) When grown for 4 days at 30° C. on Oxoid CM3 Nutrient agar and viewed by Grams stain:
   Shape—unicellular cocci.
   Association—singly and as aggregates.
   (In general, the strain appears to grow as unicellular cocci on aged cultures but as rod-shaped cells with some branching when added to fresh media).

2. Colonial morphology.
On glucose agar incubated for 4 days at 30° C.:
   Shape—round.
   Size—1 mm diameter.
   Nature—regular and entire.
   Elevation—convex with central depression.
   Pigment—cream.
   Consistency—dry.
   Emulsifiability—difficult to emulsify in water.

3. Physiological and biological tests
(a) Growth in Nutrient agar—good growth (white lawn). [Very good growth on yeast extract—malt extract agar (orange/cream wrinkled colonies)].
(b) Growth in Nutrient broth—good growth.
(c) Temperature conditions—no growth at 37°, 41° or 45° C., good growth at 28°-30° C., growth at 20° C. and some growth at 5° C. after 7 days.
(d) Relation to oxygen—aerobic.
(e) Catalase test—positive.
(f) Oxidase test (Kovac's)—negative.
(g) Glucose PWS test—negative.

This micro-organism NCIB 11880 per se forms a further subject of the present invention.

It may be provided in specific forms such as freeze dried, in composition with a solid or liquid diluent or as a culture in a culture medium eg. containing a source of assimilable carbon, a source of nitrogen and, if desired, vitamins and inorganic salts and/or substantially free from other micro-organisms.

The microbiological characteristics of this strain place it in the genus Rhodococcus sp. according to a preliminary study carried out by the NCIMB. Irrespective of its strict name, the micro-organism is adequately identified by the properties given here and the details of the deposit made at the NCIMB.

Other microorganisms which are known to have the necessary properties for performing the inversion are *Rhodococcus rhodochrous* (ATCC 13808), a Rhodococcus sp. (NCIB 11276), *Botrytis cinerea* (ATCC 28387), *Arthrobacter simplex* (NCIB 8929), *Arthrobacter roseoparaffinus* (ATCC 15584), *Bacillus subtilis* (ATCC 15841), *Brevibacterium butanicum* (ATCC 21196), *Brevibacterium healii* (ATCC 15527), *Brevibacterium ketoglutamicum* (ATCC 21004), *Brevibacterium paraffinoliticum* (NCIB 11160), *Corynebacterium fujiokense* (ATCC 21496), *Mycobacterium petroleophilum* (ATCC 21497), *Mycobacterium smegmatis* (ATCC 19420), *Nocardiopsis asteroides* (ATCC 21943), *Rhodococcus rhodochrous* (NCIB 11273), *Nocardia opaca* (NCIB 9409), *Rhodococcus* sp. (ATCC 21337), *Pseudomonas diminuta* (NCIB 9393) and *Pseudomonas lemoignei* (NCIB 9947).

The exact method of contacting the [S] enantiomer (usually in a mixture with the R enantiomer) with the microorganism or extracted enzyme system may be chosen for convenience. Clearly the contact must be of sufficient duration for the transformation (inversion) to occur. Preferably, where the contact is with immobilised whole cells, these are packed into a column and the [S] enantiomer passed through the column either in a batchwise or preferably, a continuous or semi-continuous process with the inverted [R] enantiomer being recovered at the bottom of the column. The column dimensions, rate of flow, substrate concentration, solvent and conditions of temperature and pH can be selected to give optimum yield of the [R] enantiomer. If live cells are used, the [S] enantiomer may also be separated in a column process or alternatively may be added to the culture and the product separated batchwise from the culture after a suitable period. Generally, the temperatures employed will be in the range 20° to 45° C., preferably 28° to 37° C., especially about 32° C., while the pH will generally be 5 to 9, preferably 6 to 7.5, especially 6.8 to 7.2.

The [R] enantiomers of formulae II to IX produced by the process of this invention are active herbicides and are particularly useful in post-emergence control of graminaceous weeds in broad-leafed crops. However, even where the free acid forms of the enantiomers are themselves active herbicides, it may be desirable to subject them to a further process step before utilising them for that purpose either to increase their activity or eg. to render them more capable of being taken up by the weeds they are intended to kill. Such a further process step may for example be a salification or esterification where the compound has undergone inversion in the form of its acid. The acids of formulae II to IX are preferably esterified to produce the preferred esters indicated hereinbefore. Particular examples of esterification are alkylation of 2[4(5-trifluoromethylpyridyl-2-oxy)phenoxy]propionic acid and 2[4(3-chloro-5-trifluoromethylpyridyl-2-oxy)phenoxy]propionic acid, in particular to make the n-butyl ester of the former and the methyl, propyl or ethoxyethyl ester of the latter.

The direct or indirect products of the present inversion process are capable of inhibiting the growth of unwanted graminaceous plants when applied in a herbicidally effective amount, and, in particular, can inhibit the growth of graminaceous weeds among dicotyledonous crop plants if applied to the area of a crop in an amount sufficient to inhibit the growth of the weeds but insufficient to damage the crop substantially.

The rate at which the compounds are usually applied in inhibiting the growth of weeds will depend upon factors such as the identity of the particular graminaceous weeds and broad-leafed crop, but in general 0.025 to 2.5 kg per hectare is suitable, with 0.1 to 1 kg per hectare being preferred.

The direct or indirect products are usually applied in herbicidal compositions, comprising the products as active ingredient together with a suitable solid or liquid diluent and optionally a further herbicidal compound or compounds, either having a similar spectrum of activity or a complementary activity to that of the first active compound.

The invention is illustrated by the following Examples.

EXAMPLE 1

A pure liquid culture of NCIB 11880 was grown aerobically in the dark in dextrose-peptone broth medium at 28° C. using an orbital shaker at 200 rpm. After 2 days, RS 2[4(5-trifluoromethylpyridyl-2-oxy)phenoxy]propionic acid (100 μg) was inoculated into the culture and after a further 3 days the product was stereoselectively analysed by high performance liquid chromatography (HPLC) using a method based on that of Y Tapuhi et al. in J. Chromatography 205 325-337.

After the 3 day reaction, inversion of the [S] enantiomer in the original racemate to the [R] enantiomer was found to be essentially 100% with a virtually quantitative recovery of product.

EXAMPLE 2

Cells of NCIB 11880 were immobilised in a calcium alginate gel matrix and tested, as in Example 1, for their ability to invert [S]-2[4(5-trifluoromethylpyridyl-2-oxy)phenoxy]propionic acid. The activities of the freshly prepared immobilised cells (~5% wet cells in calcium alginate) and a suspension of cells in CaCl$_2$ solution were compared to that of a viable culture containing (initially) the same quantity of microbial biomass. The systems all showed activity and exhibited pseudo first other kinetics (t$_{\frac{1}{2}}$ values for the immobilised, suspended and cultured cells were approximately 8, 6 and 4 hours respectively).

Again the recoveries of the enantiomeric product were virtually quantitative (greater than 95%) based on the quantity of racemic substrate added to the system.

EXAMPLE 3

Example 1 was repeated using as substrate RS 2[4(3-chloro-5-trifluoromethylpyridyl-2-oxy)phenoxy]propionic acid. The analogous inversion of the [S]-enantiomer was observed and the rate and extent of the reaction were similar.

EXAMPLE 4

A 50 μg/ml solution (A) of RS 2[4(5-trifluoromethylpyridyl-2-oxy)phenoxy]propionic acid in dextrose-peptone broth was prepared and a plate culture of *Rhodococcus rhodochrous* (ATCC 13808) was grown for 2 days in dextrose-peptone broth at 37° C. without shaking. 2 ml of the solution (A) was transferred to a sterile test base and innoculated with the microorganism culture via a sterile loop which was then further incubated at 37° C. for 7 days.

After the 7 day reaction, 1 ml of the solution was removed and the product stereoselectively analysed as indicated in Example 1. The percentage [R] enantiomer in the product was found to be 87%.

EXAMPLE 5

The procedure of Example 4 was repeated but using the following microorganisms to give the indicated percentage [R] enantiomer in the products. (The reaction temperature was, however, 28° C. rather than 37° C. except in the case of the asterisked microorganisms).

|  | %[R] enantiomer |
|---|---|
| Rhodococcus sp. (NCIB 11276) | 100% |
| *Botrytis cinerea* (ATCC 28387) | 92% |
| *Arthrobacter simplex* (NCIB 8929) | 58% |
| *Arthrobacter roseoparaffinus* (ATCC 15584) | 75% |
| *Bacillus subtilis* (ATCC 15841) | 62% |
| *Brevibacterium butanicum* (ATCC 21196) | 93% |
| *Brevibacterium healii* (ATCC 15527) | 79% |
| *Brevibacterium ketoglutamicum* (ATCC 21004) | 57% |
| *Brevibacterium paraffinoliticum* (NCIB 11160) | 90% |
| *Corynebacterium fujiokense* (ATCC 21496) | 100% |
| *Mycobacterium petroleophilum* (ATCC 21497) | 84% |
| *Mycobacterium smegmatis* (ATCC 19420) | 69% |
| *Nocardia opaca* (NCIB 9409) | 100% |
| *Nocardiopsis asteroides* (ATCC 21943) | 89% |
| *Pseudomonas diminuta* (NCIB 9393) | 64% |
| *Pseudomonas lemoignei* (NCIB 9947) | 73% |
| *Rhodococcus rhodochrous* (NCIB 11273) | 58% |
| Rhodococcus sp. (ATCC 21337) | 73% |

EXAMPLE 6

The procedure of Example 4 was repeated using the substrates and microorganisms indicated below to give the indicated percentage [R] enantiomer in the products.

| Substrate | Microorganism | % [R] enantiomer |
|---|---|---|
| A | Rhodococcus sp. [NCIB 11276] | 100% |
| A | Rhodococcus sp. [NCIB 11880] | 100% |
| B | Rhodococcus sp. [NCIB 11276] | 100% |
| B | Rhodococcus sp. [NCIB 11880] | 100% |

Key:
A = 2-[4-(6-chloro-2-quinoxalinyloxy)phenoxy]-propionic acid
B = 2-[4-(6-chloro-2-benzthiazolyloxy)phenoxy]-propionic acid

I claim:
1. A process for the stereospecific inversion of the enantiomer of an α-aryloxypropionic acid of formula I:

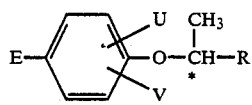

wherein E is OR[1] or

R[1] is an unsubstituted or substituted aryl or heterocyclic ring system, and R[2] is hydrogen or methyl, U and V each independently represent hydrogen or halogen and R is a carboxyl group, or an enzymic and herbicidal equivalent thereof, in a mixture with its [R] enantiomer, which process comprises contacting said [S] enantiomer with a stereospecific inverting enzyme so as to convert the [S] enantiomer to the corresponding [R] enantiomer without substantially affecting the [R] enantiomer in said mixture.

2. A process according to claim 1 wherein the enzyme comprises a bacterium.

3. A process according to claim 2 wherein the bacterium is chosen from the Actinomycetales organisms.

4. A process according to claim 3 wherein the bacterium is a Rhodococcus.

5. A process according to claim 1 wherein the enzyme comprises:

a Rhodococcus sp. (NCIB 11880), *Rhodococcus rhodochrous* (ATCC 13808), a Rhodococcus sp. (NCIB 11276), or *Botrytis* cinerea (ATCC 28387).

6. A process according to claim 1 wherein the enzyme comprises:

*Arthrobacter simplex* (NCIB 8929), *Arthrobacter roseoparaffinus* (ATCC 15584), *Bacillus subtilis* (ATCC 15841), *Brevibacterium butanicum* (ATCC 21196), *Brevibacterium healii* (ATCC 15527), *Brevibacterium ketoglutamicum* (ATCC 21004), *Brevibacterium paraffinoliticum* (NCIB 11160); *Corynebacterium fujiokense* (ATCC 21496), *Mycobacterium petroleophilum* (ATCC 21497), *Mycobacterium smegmatis* (ATCC 19420), *Nocardiopsis asteroides* (ATCC 21943), *Rhodococcus rhodochrous* (NCIB 11273), *Nocardia opaca* (NCIB 9409), Rhodococcus sp. (ATCC 21337), *Pseudomonas diminuta* (NCIB 9393) or *Pseudomonas lemoignei* (NCIB 9947).

7. A process according to claim 1 wherein the α-aryloxypropionic acid is of formula II

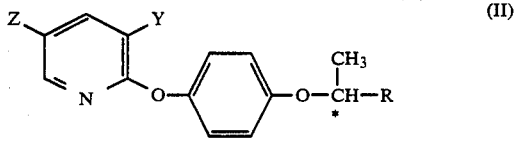

wherein Z and Y each represent fluorine, chlorine, bromine, iodine or hydrogen or a trifluoromethyl, difluoromethyl or chlorodifluoromethyl group provided that at least one of Z and Y is a halogenomethyl group and R represents a carboxyl group.

8. A process according to claim 1 wherein the process is applied to 2[4(5-trifluoromethylpyridyl-2-oxy)-phenoxy]propionic acid or 2[4(3-chloro-5-trifluoromethylpyridyl-2-oxy)phenoxy]propionic acid or an ester thereof.

9. A process according to claim 1 wherein the α-aryloxypropionic acid is of formula III

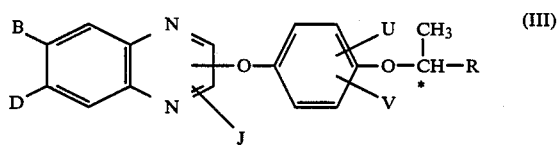

wherein B, D, J, U and V each represent hydrogen or halogen and R is a carboxyl group.

10. A process according to claim 9 wherein one of B and D is chloro, and the other hydrogen, U is hydrogen or 2-fluoro and J and U each represent hydrogen.

11. A process according to claim 1 wherein the enzyme is immobilised and contained in a column through which the [S] enantiomer is passed.

12. A process according to claim 1 wherein the [S] enantiomer is provided with the corresponding [R] enantiomer in the form of the racemate.

13. A process according to claim 1 wherein the product of the stereospecific inversion is in the form of free acid and this is subsequently esterified.

* * * * *